United States Patent
Barghelame

(10) Patent No.: US 9,629,778 B2
(45) Date of Patent: Apr. 25, 2017

(54) COLLAPSIBLE MULTI FUNCTION SAUNA AND DRYER

(71) Applicant: Si Barghelame, Woodinville, WA (US)

(72) Inventor: Si Barghelame, Woodinville, WA (US)

(*) Notice: Subject to any disclaimer, the term of this patent is extended or adjusted under 35 U.S.C. 154(b) by 103 days.

(21) Appl. No.: 13/901,439

(22) Filed: May 23, 2013

(65) Prior Publication Data

US 2014/0345041 A1    Nov. 27, 2014

(51) Int. Cl.
| | | |
|---|---|---|
| *A61H 33/06* | (2006.01) | |
| *A61N 5/06* | (2006.01) | |
| *E04H 1/12* | (2006.01) | |
| *D06F 58/14* | (2006.01) | |
| *D06F 73/02* | (2006.01) | |
| *D06F 58/28* | (2006.01) | |

(52) U.S. Cl.
CPC ..... *A61H 33/066* (2013.01); *A61H 2033/068* (2013.01); *A61H 2201/0161* (2013.01); *A61H 2201/0188* (2013.01); *A61H 2201/0207* (2013.01); *A61H 2201/10* (2013.01); *A61H 2201/5064* (2013.01); *A61H 2230/505* (2013.01); *A61N 2005/0659* (2013.01); *A61N 2005/0663* (2013.01); *A61N 2005/0668* (2013.01); *D06F 58/14* (2013.01); *D06F 73/02* (2013.01); *D06F 2058/2841* (2013.01); *E04H 2001/1288* (2013.01)

(58) Field of Classification Search
CPC . A61H 33/067; A61H 33/06; A61H 2035/004
USPC ...................................................... 4/524–534
See application file for complete search history.

(56) References Cited

U.S. PATENT DOCUMENTS

| | | | | |
|---|---|---|---|---|
| 348,923 | A | * | 9/1886 | Munro ............................... 4/524 |
| 1,549,384 | A | * | 8/1925 | Rosenthal ......................... 4/526 |
| 3,515,849 | A | * | 6/1970 | Math ............................. 219/213 |
| 4,773,105 | A | * | 9/1988 | Toyoshima ....................... 4/526 |
| 6,510,565 | B1 | * | 1/2003 | Zwezdaryk ....................... 4/531 |
| 2004/0030371 | A1 | * | 2/2004 | Barghelame .................... 607/96 |
| 2006/0064815 | A1 | * | 3/2006 | Guerin et al. .................... 4/596 |
| 2007/0050903 | A1 | * | 3/2007 | Sappenfield et al. ............. 4/524 |
| 2009/0056009 | A1 | * | 3/2009 | Matsubara et al. ............... 4/524 |
| 2010/0037385 | A1 | * | 2/2010 | Hoernig et al. ............... 4/578.1 |
| 2011/0046702 | A1 | * | 2/2011 | Duncan .......................... 607/96 |
| 2012/0304374 | A1 | * | 12/2012 | Amendt ........................... 4/524 |

FOREIGN PATENT DOCUMENTS

DE    19856554 A1 *    6/2000

OTHER PUBLICATIONS

Translation of DE 198 56 554.*

* cited by examiner

*Primary Examiner* — Lauren Crane
(74) *Attorney, Agent, or Firm* — Steinberg Intellectual Property Law LLC; Gloria M. Steinberg, Esq.

(57) ABSTRACT

A sauna cabin enclosure comprised of two half cabins, one half being smaller than the other, such that one half can fit inside the other and can slide to contract or expand partially or fully, thereby increasing or decreasing the air volume inside and the overall external size. This cabin has infrared heating, full spectrum lighting and a steam generator. When the cabin size is reduced by means of a hand crank or a motor, the air volume inside the cabin is decreased, allowing air temperature to increase proportionally. The cabin can be compressed together to minimize required floor space.

17 Claims, 4 Drawing Sheets

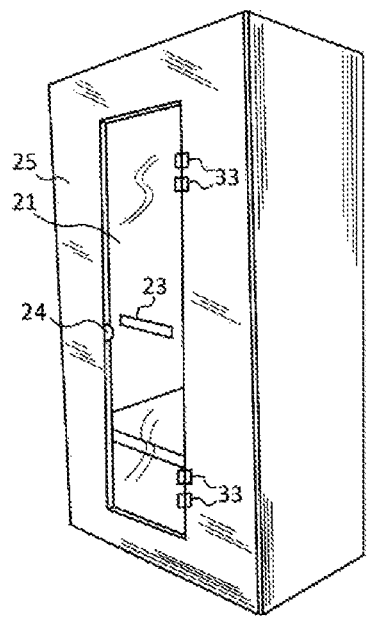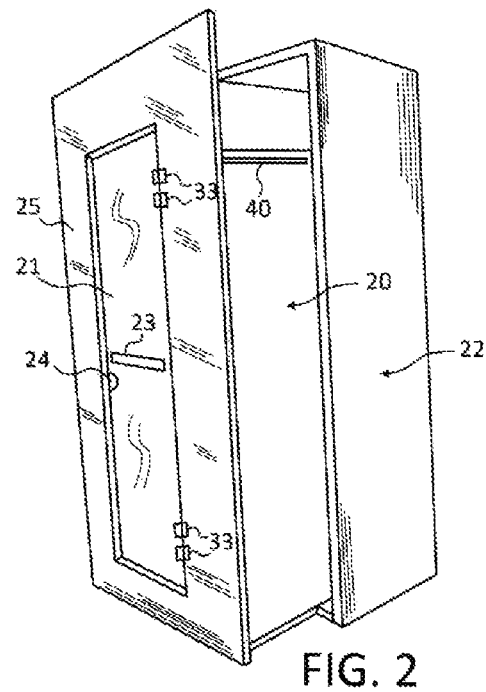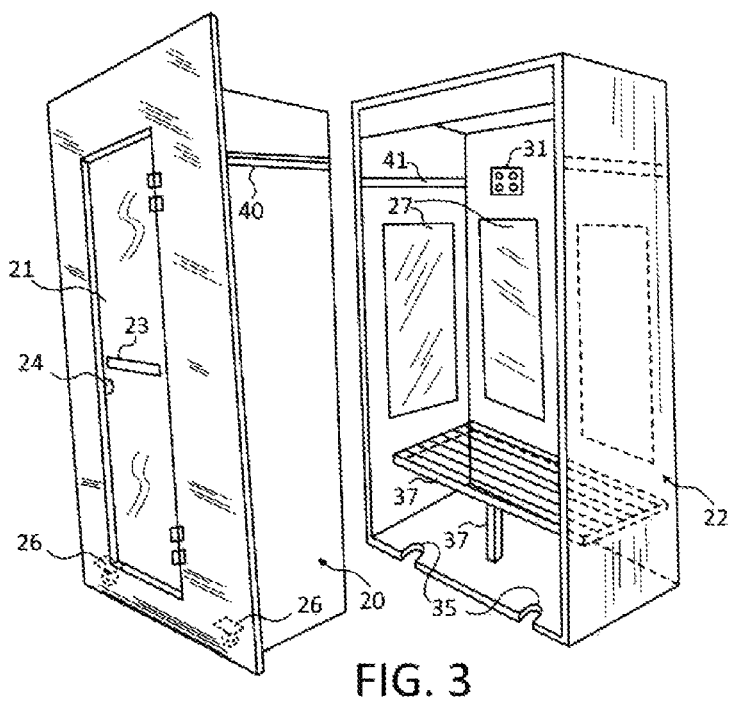

COLLAPSIBLE MULTI FUNCTION SAUNA AND DRYER

FIELD OF INVENTION

This invention is a multipurpose collapsible and expandable device useful as an infrared sauna and steam room and as a dryer and/or steam processing of clothing and other linen articles. This invention is also related to a collapsible enclosure with heat and light emitting devices, where heaters and light sources are placed within an enclosure to provide heat and light for the purpose of a sauna, and drying objects or simply heating a given space.

This invention further is generally related to heat emitting devices as space heaters or infrared sauna heaters where several or a single heaters are placed within a room, office divider or a sauna enclosure to provide heat for the person or persons using the sauna from multitude of directions and distances.

GENERAL BACKGROUND

It is well known to have a wood, metal or plastic cabin where infrared heat emitting devices are attached to or embedded in the walls of such enclosure for the purpose of providing heat to a person in order to promote sweating and a leisure experience known as a sauna. Such cabins are generally made of rigid panels assembled to create a cabin where heating elements are present. Such cabins are usually made to be a specific size with a given width, depth and height. These cabins with a fixed size and shape are then placed in a desired place within a room or office to be used as a sauna cabin. This type of sauna cabin does not allow the user to change the interior or the exterior size of the cabin for the purpose of reducing the cubic feet volume of air within the cabin enclosure as well as the exterior footprint of the cabin.

It is also the state of the art that heat emitting elements in infrared saunas are generally attached to or embedded in the walls to provide heat to the user at a constant temperature and intensity.

It also is known to provide heat in a sauna chamber, office enclosure or a room, to a person or persons by placing a heat emitting apparatus at a distance from the person to provide heat for the purpose of producing sweat or simply staying warm. Such heating articles emit heat at a constant temperature regardless of the distance, temperature or the position of the person receiving the heat. Inevitably, when multiple heaters placed at a certain distances from the person all emitting heat at constant temperature, the recipient of heat will feel higher temperatures from the elements placed at a closer distance than from the elements that are at a further distance from the person. This will normally cause "hot and cold spots" on the user's body, where certain areas of the recipient's body are warmer than other areas. To find a comfortable position, the person must constantly change position and distance from the heat emitting device. If the person desires to reduce or increase the intensity of heat received from the device, he will have to manually manipulate the control switch until a desirable intensity is found, or physically move away from or closer to the heating device. Existing heat emitting devices will stay on and produce constant temperature until changed manually or by a timer, and are unaffected by the recipient's distance, position or body temperature.

SUMMARY OF THE INVENTION

This invention provides a sauna cabin that allows the user to increase or decrease the interior volume and exterior size of the sauna cabin as desired. The variable volume may reduce power consumption, minimize storage space, provide quicker heating time, and easier transportation. By allowing the user to adjust the interior air volume of the cabin, it is possible for the user to achieve a higher temperature or reach the desired temperature inside the cabin within a shorter amount of time. These increased temperatures and faster heating times will be achieved while consuming less electric power, therefore operating more economically. It is also common practice that when a sauna cabin is not in use it sits idle and occupies space that cannot be used for any other purpose. This invention provides the capability of the cabin to be retracted and occupy less floor space, and to be used as a dryer, for steam pressing and sanitizing clothing and other articles such as linens and foods.

This invention has added a multitude of sensors that can sense and control the intensity of each heater, providing the user more even heating and a more pleasant sauna experience. These sensors are placed strategically within the sauna cabin in order to sense movement, distance and body temperature of the person inside the sauna and to automatically adjust the heat intensity according to the signals received from said sensors. The sensors also provide an even heating capability in order to provide an even drying of the clothing or other linen articles, therefore eliminating wet and dry blotchy clothing and uneven wrinkling on the clothing.

This invention has also a provision for eliminating EMF (Electro Magnetic Field) which is common in infrared saunas, therefore providing a healthier sauna atmosphere for the user.

The cabin is made of two separate half cabins, where one half can fit tightly into the second half by means of a sliding mechanism and/or rollers and casters. Having two independent half-structures makes it possible to alter the interior cubic feet of air volume inside the cabin enclosure, and provides for easier shipping and handling. This design also allows the entire cabin to be assembled by anyone with minimal tools and no training. After the two halves are assembled together, the cabin can be extended partially or fully as desired by the user. When the two half cabins are in the fully extended position, the inside air volume is at its maximum capacity. As the two halves of the wooden cabin contract, the cubic air volume is reduced, creating a smaller cubic feet of air volume, allowing the existing heat emitting elements to heat the cabin to a higher temperature within a shorter amount of time. The cabin enclosure also serves as a dryer and steam room for unwrinkling or steam pressing clothing and linen articles. A foldable bench mechanism is attached to one of the walls for easy folding. A flat gear and a circular gear mechanism provide an easy way to extend or contract the two separate halves of the cabin. It also provides a means to expand the two halves fully or partially to create a desired interior size and to reduce or increase the air volume.

The sauna cabin is heated with infrared heating elements that are attached or embedded in the walls of the enclosure. The cabin has at least one door for access inside and a bench to allow a person to sit or lie down. The bench in the cabin is assembled by a hinge system that can be folded so that the cabin can be collapsed to become smaller in depth and therefore able to be maneuvered through tight quarters and fit into smaller areas such as a closets, small bathrooms, bedrooms, and into apartments or condos. When the bench is in its folded position against the back wall it will not interfere with the clothing articles that require a taller area for drying and steam pressing and un-wrinkling purposes. This cabin also includes a retractable clothes-line for the purpose of hanging and drying clothing or linen articles. The cabin is also equipped with a steam generating apparatus that can introduce steam inside the enclosure for the purpose of steam pressing and un-wrinkling clothing or linen articles, and to provide steam for the user in order to promote sweating. Both the collapsed or fully extended position allow the sauna enclosure to be used as a dryer room for clothing, linen, and other items that need to be dried, steamed and/or sanitized.

This cabin is also equipped with at least one fan system to create and control the movement of the air within the sauna enclosure.

The infrared heating elements in this cabin are equipped with sensors that measure the distance, motion, and body or surface temperature of the person and/or objects such as clothing or linen receiving the heat, in order to provide evenly distributed and safer heating for the person or aforementioned objects. The sensors for body temperature, surface temperature and distance will adjust the intensity of heat in the sauna enclosure and the sauna sensory system will sense the clothing article moisture content again for the purpose of evenly distributed drying. The sensors are use also to provide safety when using the space as a dryer or as a sauna room.

This cabin has at least one full spectrum lighting system and a color changing LED lighting system to provide the user of the sauna with light therapy and chromo-therapy, providing the user with multiple health benefits such as relief from SAD (Seasonal Affective Disorder). Also the cabin has a UV bulb that emits ultraviolet light to provide the user with ultraviolet light therapy. The UV light will also be used to sanitize the clothing and linen articles that are being dried or unwrinkled. The UV bulb will also sanitize and deodorize the sauna enclosure after each use. The UV bulb in the sauna enclosure is connected to a timing device that regulates the amount of time the UV bulb can be on. The timing device is used to prevent the sauna user or the articles of clothing or linens from over exposure to the UV light while inside the sauna cabin enclosure.

This cabin is equipped with smooth sliding footing surfaces or rollers that are adjustable for height underneath the base of the cabin structure. These provide a level installation and easy mobility in a room for relocating, moving or cleaning under or around the unit.

The exterior walls of the cabin can be covered with easily removable decorative panel coverings made of wood or other materials to provide a desirable and customizable look to match any room decor and color combination.

The infrared heating elements and the lighting system inside this cabin are covered with a specially designed conductive metal grid that can be grounded with a grounding wire to reduce the EMF (Electro Magnetic Frequency) production within the cabin enclosure. This will provide a healthier space for the user.

Heat intensity emitted by each heater is constantly changing automatically, controlled by the signals sent by each sensor on or near the heaters. If a person or clothing article is moved closer to a heating apparatus, the heat emitted by that element will be automatically reduced to compensate for the shorter distance between the person or object and the heater. The same principle is applied when a person or a clothing article has moved away from a particular element in that the intensity of heat emitted from that element will increase accordingly to compensate for the distance between the person and the heating element.

The cabin will also automatically self adjust the intensity of heat emitted from each heater in accordance with the body temperature of the person in front of that heater. This is actuated by the appropriate body temperature sensor on or near the particular heating apparatus.

The motion sensors on or near the heaters will also affect the operation of the heating apparatus.

When two halves of the cabins start contracting from its fully extended position by means of the hand cranked or motorized gear mechanism, the distance between the person sitting inside the cabin and the front heat emitting elements are reduced, therefore the person will feel a higher intensity of heat. The user of the sauna can adjust this distance to a desired position.

BRIEF DESCRIPTION OF DRAWINGS

FIG. 1 is a front perspective view of a sauna cabin constructed according to the teachings of this invention in a stowed position;

FIG. 2 is a front perspective view of a sauna cabin constructed according to the teachings of this invention in an extended position;

FIG. 3 is an expanded perspective view showing the front portion of the cabin extended from the back portion of the cabin;

DETAILED DESCRIPTION OF THE PREFERRED EMBODIMENT

Figure 7:
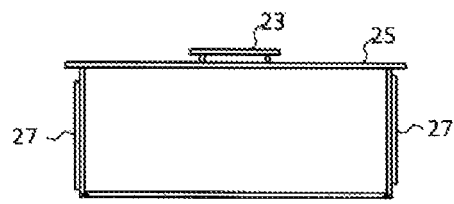
FIG. 7 is a top view of the sauna in stowed position.

Referring specifically to the drawings wherein like numerals indicate like parts, FIGS. 1-3 show perspective views of a sauna cabinet according to the present invention. The sauna cabinet comprises a front cabinet 20 and a rear cabinet 22. The front cabinet 20 comprises a front wall having sidewalls, a top wall, and a bottom wall extending rearwardly therefrom. The sidewalls, top, and bottom walls of the front cabinet 20 is oriented closer towards the bottom end than the upper end of the front wall of the front cabinet 20. The rear cabinet 22 comprises a backwall having sidewalls, a top wall, and a bottom wall extending forward therefrom. FIG. 1 shows the sauna in its collapsed position with front cabinet 20 inserted fully within rear cabinet 22, resulting in a minimum footprint for the sauna cabinet, typically when the sauna is not in use or when the sauna cabinet is in use for drying clothing or other products. When fully collapsed, the perimeter edge of the front wall of the front cabinet 20 can directly contact terminal edges of the sidewalls, top wall, and the bottom walls of the rear cabinet 22. FIG. 2 shows the sauna in its extended position with the front cabinet portion 20 fully extended but still an operative connection with rear cabinet 22. The front wall of the front cabinet 20 has a glass access door 21 mounted on hinges 33. A door handle 23 provides a convenient means to open and close door 21. A magnetic door latch 24 is provided to maintain the door 21 in a closed position. In FIG. 3 the front cabinet 20 and rear cabinet 22 are shown disengaged from each other to permit a view of the interior of the rear cabinet 22 which has mounted therein heater panels 27, heat sensor 31, and bench 36 which is hinged to the back of rear cabinet 22 and supported by bench support 37 slots 35 are shown cut in the lower portion of rear cabinet 22 to accommodate rollers 26. Support slides 40 are positioned on each exterior side of front cabinet 20 designed to travel within and engage support grooves 41.

Figure 4:
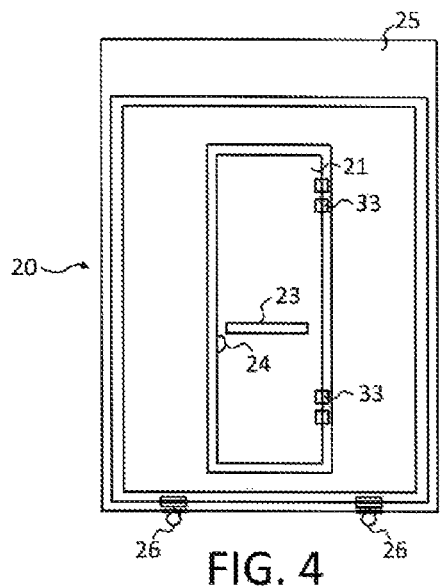
FIG. 4 is a front elevation overview of the sauna of this invention.

FIG. 4 shows a front elevational view of the front cabinet 20 in which rollers 26 are shown positioned at the bottom thereof to support and permit movement in and out of the front cabinet 20 from rear cabinet 22 from its stowed position shown in FIG. 1 to the fully extended position shown in FIG. 2.

Figure 5:
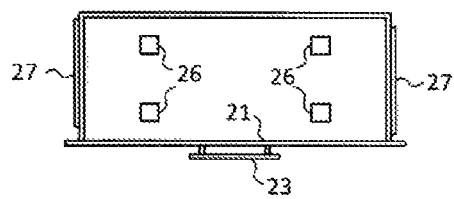
FIG. 5 is a bottom plan view of the sauna of this invention in the stowed or compressed configuration.

FIG. 5 is a bottom view of front cabinet 20 showing the location of rollers 26. Heater panels 27 are shown positioned on each side of front cabinet 20.

Figure 6:
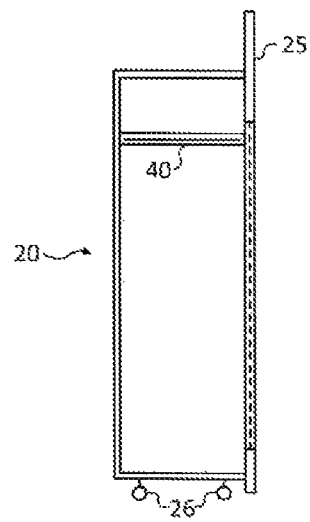
FIG. 6 is a side elevational of the front or extendable portion of the sauna cabin.

FIG. 6 is a side view of front cabinet 20 showing the location of support slides 40 extending from front surface 25 to the back of front cabinet 20.

Figure 10:
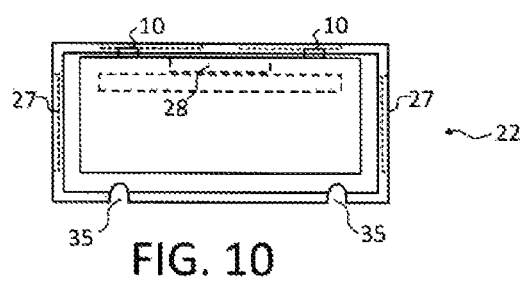
FIG. 10 is a top cross sectional view taken along lines 10-10 of FIG. 8.
Figure 8:
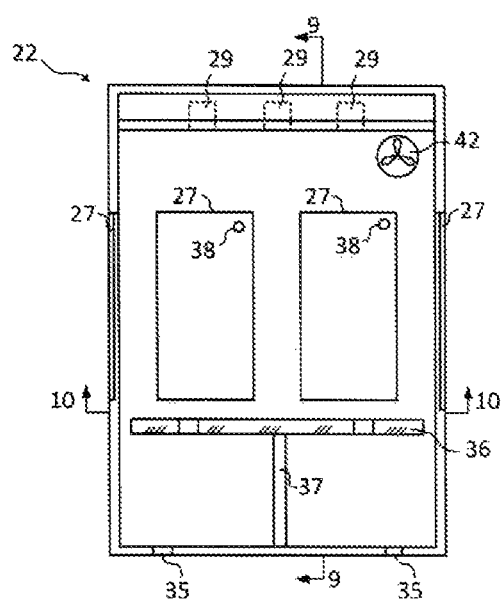
FIG. 8 is a front elevational view of the interior of the rear portion of the sauna cabinet showing the bench, heating units, fan and lighting units.
Figure 9:
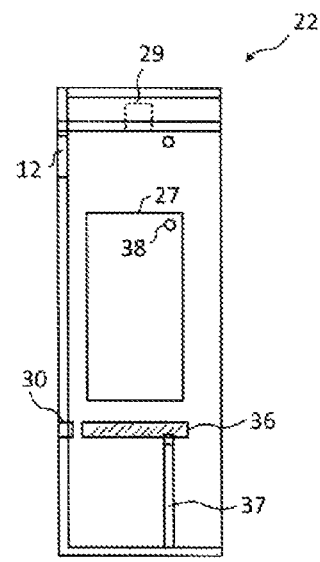
FIG. 9 is a side elevational view in section taken along lines 9-9 of FIG. 8 of the rearward portion of the sauna cabinet.

In FIGS. 8, 9 and 10 the rear cabinet 22 is shown having bench 36 pivotally mounted on the back thereof at hinge 30 and supported by bench support 37. Heater panels 27 are shown positioned in the back and sides of rear cabinet 22. Full-spectrum lighting is provided by bulbs 29 in the ceiling of rear cabinet 22. The air inside rear cabinet 22 is circulated by fan 42. Sensors 38 permit accurate reading of temperature, motion detection and other operating parameters of the sauna for the consistent heating and comfort of the occupants. To accommodate the wheels or rollers which carry front cabinet 20, slots 35 are provided in the floor of rear cabinet 22.

The heat emitting apparatus 27 may be equipped with proximity sensors 38 for distance, motion sensor for movement and surface temperature sensor for sensing the surface temperature of a person or a textile article that is being dried. The apparatus includes a heating element 27 for emitting heat, and a sensor 38 positioned to receive signals from a person or an article inside the sauna enclosure. Power supplied to the heating element 27 is constantly adjusted independent of other heaters, according to the signals and the data provided by the proximity, motion and remote temperature sensors, affected by signals received from all or at least one of the sensors. The emitter is constantly adjusting the heat emitted accordingly. This adds to safety and more even heating capability, eliminating the need for constantly adjusting manually, or constantly moving and changing location to feel comfortable. Safety and economy is further enhanced since the emitter will turn itself off if there is no motion detected for a specified period of time, or an article is touching or is in a too close of proximity that can cause burns or fire hazard.

The collapsible sauna described above is normally in the fully retracted position when not in use with front cabinet 20 positioned inside rear cabinet 22. To set up the sauna for use, front cabinet 20 is manipulated into the fully extended position shown in FIG. 2. It is contemplated that the movement of front cabinet 20 with respect to rear cabinet 22 may be accomplished manually or the device may be provided with a manual or motor driven drive mechanism to move the front cabinet into its extended position and to return it partially or completely into the retracted position shown in FIG. 1.

Figure 11:
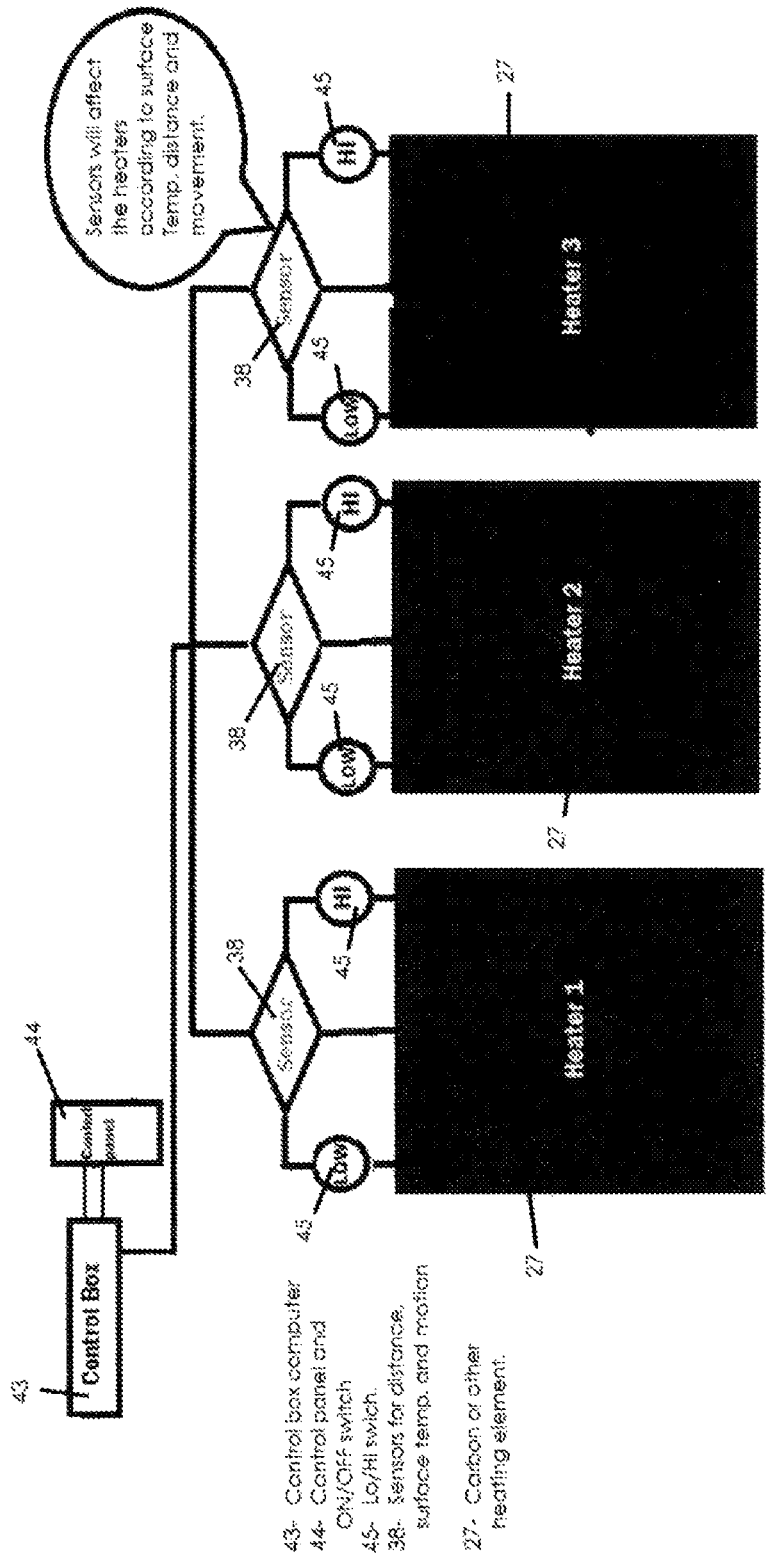
FIG. 11 is a schematic view of a flow chart showing operation of the heating system and its controls for the heaters in the sauna cabinet.

FIG. 11 is a diagram of the flow chart showing the information sent by the sensor 38 attached on each and every heating elements providing a way of controlling and adjusting temperature on individual heat emitting element. Sensors will sense and send signals for ambient temperature, distance, motion and surface temperature.

In an alternate embodiment, the rear cabin may be configured and designed to fit inside the front cabin.

This invention also contemplates a method of operating a collapsible sauna structure comprising a rear cabinet, a front cabinet nesting within said rear cabinet, said front cabinet having support elements permitting movement of said front cabinet from a rest position within said rear cabinet to an extended position extended forwardly from said rear cabinet, said method comprising the steps of moving said front cabinet from a stored position to an extended position, operating the sauna functions to provide a heated space with full-spectrum lighting for one or more occupants, discontinuing the sauna functions, and returning the front cabinet to its stored position. Is also contemplated that the sauna device of this invention may be operated at various partially extended positions to effectively modify the total volume of gas present within the sauna during its operations. In this way the interior of the sauna may be heated more rapidly due to the smaller volume of air present within the sauna structure.

The present invention is described above primarily for use as an electrical powered, full-spectrum light sauna for use by one or more individuals but may also be used in the drying or maintenance of clothing and foods. The foregoing has been a description of certain preferred embodiments of the present invention but is not intended to limit the invention in any way. Rather, many modifications variations and changes in details may be made within the scope of the present invention.

I claim:

1. A collapsible sauna having rigid sidewalls, comprising:
a rear sauna cabinet having a back wall with sidewalls, a top wall, and a bottom wall extending forward from said back wall;
a front sauna cabinet having a front wall with an access door therein and having sidewalls, a top wall, and a bottom wall extending rearwardly therefrom, said sidewalls, said top wall, and said bottom wall of said front sauna cabinet oriented closer toward a bottom edge of said front wall than an upper edge of said front wall, edges of said front wall extending beyond said sidewalls of said front sauna cabinet, said top wall of said front sauna cabinet, and said bottom wall of said front sauna cabinet such that said front wall of said front cabinet can directly contact terminal edges of said sidewalls, said top wall, and said bottom wall of said rear sauna cabinet;
said sidewalls, said top wall, and said bottom wall of said front sauna cabinet configured to mate with said sidewalls, said top wall, and said bottom wall of said rear sauna cabinet to permit said front sauna cabinet to move from a stowed position to a partially or fully extended position, thereby forming a sauna cavity;
infrared heating panels positioned within said rear sauna cabinet;
a full-spectrum lighting system positioned within said rear sauna cabinet;

a pivotally mounted bench attached to said back wall of said rear sauna cabinet, said bench having a floor engaging support to hold said bench in a horizontal position for use by an occupant.

2. The apparatus of claim 1, wherein each of said sidewalls of said front sauna cabinet comprises a support slide positioned on an exterior side thereof, further wherein each of said sidewalls of said rear sauna cabinet comprises a support groove positioned on an interior side thereof;

said support slide engaging said support groove to move said front sauna cabinet from said stowed position to said partially or fully extended position.

3. The apparatus of claim 1, wherein said bottom wall of said front sauna cabinet comprises support rollers thereon.

4. The apparatus of claim 1, wherein said access door in said front sauna cabinet is a transparent panel mounted on hinges to permit access to said sauna cavity.

5. The apparatus of claim 3, wherein said bottom wall of said rear sauna cabinet comprises slots to receive said support rollers of said front sauna cabinet.

6. The apparatus of claim 1, wherein said sidewalls, said bottom wall, and said top wall of said front sauna cabinet fits within said rear sauna cabinet.

7. A method of operating a collapsible sauna structure, said sauna structure comprising a rear sauna cabinet and a front sauna cabinet nesting within said rear sauna cabinet, said front sauna cabinet having support elements permitting movement of said front sauna cabinet from a rest position nested within said rear sauna cabinet to an extended position extended forwardly from said rear sauna cabinet, said method comprising the steps of:

moving said front sauna cabinet from a stored position to an extended position, wherein said front sauna cabinet comprises a front wall having sidewalls, a top wall, and a bottom wall extending rearwardly therefrom, said sidewalls, said top wall, and said bottom wall of said front sauna cabinet oriented closer toward a bottom edge of said front wall than an upper edge of said front wall;

operating sauna functions to provide a heated space with full-spectrum lighting for one or more occupants;

discontinuing the sauna functions; and returning said front sauna cabinet to its stored position such that edges of a front wall of said front sauna cabinet directly contact terminal edges of a top wall, sidewalls, and a bottom wall of said rear sauna cabinet.

8. The method of claim 7, wherein said sauna functions comprise sensors to automatically detect temperature, body temperature of said one or more occupants inside said sauna, and motion.

9. The method of claim 7, wherein said front sauna cabinet is nested within said rear sauna cabinet, and is moveable forwardly to an operational position, thereby forming a sauna cavity.

10. The apparatus of claim 1, wherein said rear sauna cabinet further comprises a sensor.

11. The apparatus of claim 10, wherein said sensor comprises a heat sensor.

12. The apparatus of claim 10, wherein said sensor comprises a temperature sensor.

13. The apparatus of claim 10, wherein said sensor comprises a motion sensor.

14. The apparatus of claim 10, wherein said sensor comprises a proximity sensor.

15. The apparatus of claim 1, wherein said rear sauna cabinet further comprises a fan.

16. The apparatus of claim 1, wherein said rear sauna cabinet further comprises a color changing LED lighting system.

17. The apparatus of claim 1, wherein said rear sauna cabinet further comprises at least one UV bulb.

* * * * *